United States Patent [19]

Mészáros et al.

[11] 4,209,622

[45] Jun. 24, 1980

[54] 3-(ETHOXYCARBONYL-METHYL)-6-METHYL-4-OXO-6,7,8,9-TETRAHYDRO-4H-PYRIDO[1,2-A]PYRIMIDINE

[75] Inventors: Zoltan Mészáros; József Knoll; István Hermecz; Lelle Vasvári; Ágnes Horváth, all of Budapest, Hungary

[73] Assignee: Chinoin Gygyszer es Vegyeszeti Termekek Gyara Rt., Budapest, Hungary

[21] Appl. No.: 559,916

[22] Filed: Mar. 19, 1975

Related U.S. Application Data

[63] Continuation-in-part of Ser. No. 452,275, Mar. 18, 1974, abandoned.

[30] Foreign Application Priority Data

Mar. 30, 1973 [HU] Hungary ............................... GI 1361

[51] Int. Cl.$^2$ .................. A61K 31/505; C07D 487/04
[52] U.S. Cl. ..................................... 544/282; 424/251
[58] Field of Search .................. 260/256.4 F, 256.4 Q; 424/251; 544/282

[56] References Cited

U.S. PATENT DOCUMENTS

| 3,149,112 | 9/1964 | Allen | 260/256.4 Q |
| 3,585,198 | 6/1971 | Meszaros et al. | 260/251 A |
| 3,853,871 | 12/1974 | Agata et al. | 260/256.4 Q |

FOREIGN PATENT DOCUMENTS

| 2315422 | 10/1973 | Fed. Rep. of Germany | 260/256.4 F |
| 1209976 | 10/1970 | United Kingdom | 260/256.4 F |

OTHER PUBLICATIONS

Meszaros et al., "Chemical Abstracts", vol. 78 (1973), col. 43539k.

*Primary Examiner*—Donald G. Daus
*Assistant Examiner*—James H. Turnipseed
*Attorney, Agent, or Firm*—Karl F. Ross

[57] ABSTRACT

Pyrida-(1,2A)-pyrimidine-derivatives and a process for preparing these compounds are disclosed. These compounds possess analgesic, anti-inflammatory, and antipyretic properties as well as the ability to depress the central nervous system.

1 Claim, No Drawings

3-(ETHOXYCARBONYL-METHYL)-6-METHYL-4-OXO-6,7,8,9-TETRAHYDRO-4H-PYRIDO[1,2-A]-PYRIMIDINE

This application is a continuation-in-part of Ser. No. 452,275 filed Mar. 18, 1974 now abandoned.

This invention relates to new pyrido (1,2 A)-pyrimidine-derivatives and a process for the preparation thereof. The present invention also relates to pharmaceutical compositions containing these compounds.

According to a feature of the present invention, there are provided new compounds of the formula (I)

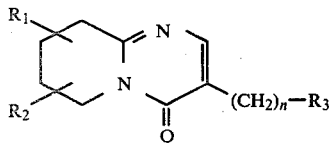

and pharmaceutically effective acid-addition and quaternary salts thereof, wherein
  $R_1$ is hydrogen or alkyl,
  $R_2$ is hydrogen, halogen, alkyl, aralkyl, amino, alkylamino, acylamino, hydroxy, alkoxy, carboxy, or a carboxylic acid derivative group,
  $R_3$ is hydrogen, carboxy or a carboxylic acid derivative group and
  $n=1$ or 2.

The term "alkyl group" relates to straight or branched chain alkyl groups, having 1–4 carbon atoms (e.g. methyl, ethyl, etc.). The term "halogen atom" covers the chlorine, bromine, fluorine and iodine atoms. The alkylamino groups may contain 1–7 carbon atoms. The acyl group of the acylamino groups may be derived from $C_{1-6}$ alkanoic acids or benzoic acid (e.g., acetyl, propionyl, benzoyl, etc.). The alkoxy groups may be straight or branched chain and may contain 1–4 carbon atoms (e.g. methoxy, ethoxy, isopropoxy, n-butoxy). The aralkyl groups may contain 7–9 carbon atoms (e.g. benzyl, beta-phenylethyl, etc.).

The carboxylic acid derivative groups encompass conventional carboxylic acid derivatives. In this context the following groups are perferable: alkoxycarbonyl groups (e.g. straight or branched chained alkoxycarbonyl groups containing 1–6 carbon atoms, such as methoxycarbonyl, ethoxycarbonyl, propoxycarbonyl, isobutoxycarbonyl, etc.), carbamoyl group, N-substituted carbamoyl groups, such as N-alkyl-carbamoyl groups or N-aralkyl-carbamoyl groups (the alkyl substituent may contain 1–6 carbon atoms, e.g. methyl, ethyl, propyl, butyl, etc.), while the aralkyl substituent may contain 7–9 carbon atoms (e.g. benzyl, beta-phenylethyl), while the aryl moiety thereof may be optionally substituted by alkyl, alkoxy or halogen substituents. Preferred substituted carbamoyl groups are the following: N-methyl-, N-ethyl- and N-2-(3,4-dimethoxyphenyl)-ethyl-carbamoyl. Further carboxylic acid derivative groups are the acid-hydrazido group and the hydroxamic acid groups.

The salts of the compounds of the formula (I) may be formed with inorganic or organic acids, such as hydrochloric acid, hydrobromic acid, phosphoric acid, sulphuric acid, perchloric acid, formic acid, acetic acid, citric acid, malic acid, glutamic acid, amygdalic acid, salicyclic acid, etc.

The pharmaceutically acceptable quaternary salts of the compounds of the formula (I) will not cause curareformparalysis and are formed with conventional quaternarizing agents, e.g. alkyl halides (e.g. methyl iodide, ethyl iodide, etc.) dialkyl sulphates (e.g. dimethyl sulphate) or alkyl- or aryl benzene sulphonates or p-toluene sulphonates.

Principally, the invention relates to a compound of the following formula:

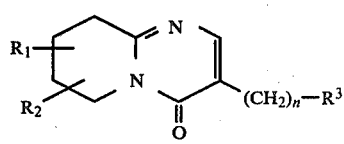

and pharmaceutically acceptable salts thereof wherein
  $R^1$ is hydrogen or $C_1$ to $C_4$ alkyl;
  $R^2$ is hydrogen, halogen, $C_1$ to $C_4$ alkyl, $C_7$ to $C_9$ arylalkyl, amino,
  $C_1$ to $C_7$ alkylamino, $C_1$ to $C_6$ acylamino, hyroxy, $C_1$ to $C_4$ alkoxy, carboxy, $C_1$ to $C_6$ alkoxy carbonyl, carboxamido, carboxamido substituted by $C_1$ to $C_6$ alkyl, carboxamido substituted by $C_7$ to $C_9$ arylalkyl, or carboxy hydrazido;
  $R^3$ is hydrogen, carboxy, $C_1$ to $C_6$ alkoxy carbonyl, carboxamido, carboxamido substituted by $C_1$ to $C_6$ alkyl, carboxamido substituted by $C_7$ to $C_9$ arylalkyl, or carbonyl hydrazido; and n is 1 or 2.

Particularly preferred representatives of the compounds of the formula (I) are the following derivatives:
3-(carboxymethyl)-6-methyl-4-oxo-6,7,8,9-tetrahydro-4H-pyrido (1,2a)pyrimidine;
3-(carboxymethyl)-4-oxo-6,7,8,9-tetrahydro-4H-pyrido(1,2a)pyrimidine;
3-(ethoxycarbonyl-methyl)-6-methyl-4-oxo-6,7,8,9-tetrahydro-4H-pyrido(1,2a)pyrimidine;
3-(ethoxycarbonyl-methyl)-7-methyl-4-oxo-6,7,8,9-tetrahydro-4H-pyrido(1,2a)pyrimidine;
3-(ethoxycarbonyl-methyl)-8-methyl-4-oxo-4H-pyrido(1,2a)pyrimidine;
6-methyl-4-oxo-6,7,8,9-tetrahydro-4H-pyrido(1,2a)-pyrimidine-3-(methyl-carbohydrazide);
3,6-dimethyl-4-oxo-6,7,8,9-tetrahydro-4H-pyrido(1,2a)-pyriimidine;
3-(N-2-phenyl-ethyl)-carboxamido-methyl-6-methyl-4-oxo-6,7,8,9-tetrahydro-4H-pyrido(1,2a)pyrimidine;
3-(N-2-(3,4-dimethoxy-phenyl)-ethyl)-carboxamido-methyl-6-methyl-4-oxo-6,7,8,9-tetrahydro-4H-pyrido(1,2a)pyrimidine, and pharmaceutically effect acid-addition salts and quaternary salts, particularly the methosulphates thereof.

According to a further feature of the present invention, there is provided a process for the preparation of compounds of the formula (I) and salts and quaternary salts thereof, which comprises subjecting a compound of the formula (II)

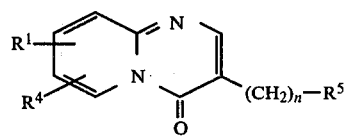

to reduction (in which formula $R^1$ and n have the same meaning as stated above, $R^4$ is as $R^2$ or stands for nitro, and $R^5$ is a carboxy or carboxylic acid derivative group) and thereby converting it to a compound of the formula (III)

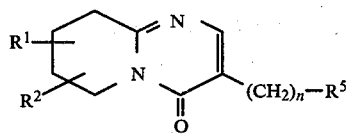

thus obtained the $R^5$ group into an $R^3$ group or if desired transforming an $R^3$ group into another $R^3$ group and if desired converting a compound of the formula (I) thus obtained into its acid addition salt or quaternary salt or setting free a compound of the formula (I) from its acid addition salt or quaternary salt.

Reduction may be preferably effected by catalytic hydrogenation. Hydrogenation may be carried out at a temperature between 0° C. and 100° C. and under atmospheric pressure or under a pressure of 1–50 atm.

The reaction is carried out in a solvent. As reaction medium water, alkanols (e.g. methanol or ethanol), esters, (e.g. ethylacetate), ketones (e.g. acetone or methyl-ethyl-ketone) or organic acids (e.g. acetic acid) or their mixture may be used.

As catalyst conventional hydrogenating catalysts may be used. It is preferred to use a palladium-on-charcoal catalyst, Raney-nickel, platina or platina oxide.

In the course of hydrogenation the pyridine ring of the starting material of the formula (II) becomes saturated by taking up 2 moles of hydrogen. After the absorption of the calculated amount of hydrogen, the catalyst is removed (preferably by filtration, centrifuging, sedimentation or decanting) and the solvent is distilled off. The compound of the formula (III) thus obtained or its acid addition salt may be recrystallized from a suitable solvent, if necessary.

If starting materials of the formula (II) are used wherein $R^4$ stands for a nitro-group; in addition to the saturation of the pyridine ring the nitrogroup is reduced too and compounds of the formula (III) are obtained, in which $R^2$ stands for an amino group. If a starting material of the formula (II), wherein $R^4$ stands for a nitrogroup, is hydrogenated in the presence of a ketone-type solvent, the amino group formed reacts with the solvent under the removal of water to yield a Schiff-base. The carbonnitrogen double bound of this compound is saturated under the hydrogenating circumstances and compounds of the formula (III) are obtained, in which $R^2$ is an alkylamino group. Thus if a starting material of the formula (II), wherein $R^4$ is a nitro-group, is hydrogenated in the presence of acetone as solvent, a compound of the formula (III) is obtained, in which $R^2$ stands for an isopropylamino group.

The $R^5$ group of the compound of the formula (III) may be converted, if desired, into the $R^3$ group of the compounds of the formula (I) or an $R^3$ group may be transformed into another $R^3$ group by means of methods known per se. Thus an alkoxycarbonyl group may be converted into the carboxyl group by means of hydrolysis. The reaction may be preferably carried out under alkaline conditions, by using an alkali hydroxide, preferably an aqueous sodium or potassium hydroxide solution. An alkoxycarbonyl group may be converted into an acid-hydrazide group by treatment with hydrazine; the latter may be preferably used in the form of an alcoholic hydrazine solution; salts and the hydrate of hydrazine may both be used. The carboxyl group may be converted into an alkoxycarbonyl group (e.g. ethoxycarbonyl group) by treating with an alcohol (e.g. ethanol) in the presence of a solvent (e.g. benzene). The carboxyl group may be transformed into an acid amide by reacting with the corresponding amine in the absence of a solvent or in the presence thereof (e.g. xylene). The free-carboxylic acid may be converted into acid chlorides by treatment with a halogenating agent (e.g. thionyl chloride, phosphorous oxychlorides, etc.). The acid halides may be converted into free acids by treatment with water, or into alkoxycarbonyl esters by treating with the corresponding alcohol, or acid amides by treatment with the corresponding amine. A compound of the formula (I), wherein $R^3$ is a carboxyl group, may be transformed into the corresponding compound of the formula (I), wherein $R^3$ is hydrogen, by decarboxylation. The reaction may be carried out by heating at a temperature above the melting point of the carboxylic acid.

The above conversions of an $R^3$ group into another $R^3$ group are carried out by conventional methods wellknown to one skilled in the art.

The compounds of the formula (I) may be converted into their acid addition and quaternary salts by methods known per se. One may proceed by reacting the base of the formula (I) with an approximately equimolar amount of the corresponding acid or quaternarizing agent in the presence of an organic solvent. As acid both organic and inorganic acids are suitable, i.e. hydrochloric acid, hydrobromide acid, phosphoric acid, sulphuric acid, perchloric acid, formic acid, acetic acid, citric acid, amygdalic acid, malic acid, glutamic acid, salicylic acid, etc. As quaternerizing agent e.g. alkyl halides (such as methyl iodide, ethyl iodide, ethyl iodide, dialkyl sulphates, e.g. dimethyl sulphate, alkyl- and arly benzene sulphonates and p-toluene sulphonates may be used).

The starting materials of the formula (II) may be prepared by subjecting a compound of the formula (IV)

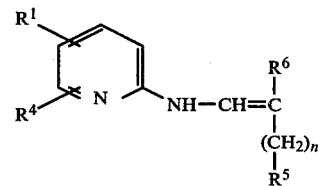

to cyclization, (wherein $R^1$, $R^4$, $R^5$ and n have the same meaning as stated above, and $R^6$ stands for an alkoxycarbonyl group). The ring closure may be carried out in the presence of an inert solvent or an acidic condensing agent (e.g. phosphorous oxychloride, phosphorous trihalides, polyphosphoric acid, etc.) at a temperature between 25° C. and 400° C. (The preparation of the starting material is disclosed in DOS 2 315 422).

The compounds of the formula (I) possess useful therapeutical properties and exhibit analgesic, antiinflammatory and antipyretic affect and exert other desired effects on the central nerval system (e.g. narcotic and tranquillant effect, etc.).

According to a further aspect of the present invention, there are provided pharmaceutical compositions comprising as active ingredient a compound of the formula (I) or an acid addition salt or quaternary salt thereof in admixture with suitable inert solid or liquid carriers or diluents. The compositions may be finished in solid (e.g. tablets, pills, coated pills, capsules, suppositories) or liquid (e.g. solution, suspension, emulsion, etc.) form.

The conventional carriers may be used such as magnesium stearate, talc, calcium carbonate, water, polyethylene glycol, glycerol-formal, etc.

The compositions may optionally contain usual additives, such as emulsifying, suspending desintegrating agents, etc.

The compounds of the formula I have a low toxicity and are very potent drugs particularly as analgesic, narcosis-potentiating, and antiinflammatory agents. The the $LD_{50}$ value of 3-(ethoxycarbonyl-methyl)-1,6-dimethyl-4-oxo-6,7,8,9-tetrahydro-4H-pyrido (1,2a) pyrimidinium-methosulphate amounts to 1500 mg/kg (s.c., on rats). According to the hot plate test the subcutaneous $ED_{50}$ value is 160 mg/kg (in rats). When administered in a dose of 120 mg/kg i.v. it proved to be active in the algolytic test and also exhibited a morphine-potentiating effect.

The compound 3-(carboxymethyl)-6-methyl-4-oxo-6,7,8,9-tetrahydro-4H-pyrido(1,2a)pyrimidine has a toxicity of higher than 2000 mg/kg (p.o., in rats). In the narcosia potentiating test the oral $ED_{50}$ value is 1000 mg/kg.

The tests were carried out by well known and generally used methods:

Hotplate Test: Woolfe and McDonald, A.P., J.Pharm. 80, (1944) 300; modifiziert durch Porszasz und Herr, F. Kiserl. Orvostud. 2, (1950) 292.

Algolytic Test: Knoll, J., in: Animal and Clinical Pharmacologic Techniques in Drug Evaluation. Eds. Siegler, P.E. and Moyer, J. II, Year Vook Medical Pub. Chicago, 1967,.

Toxicity: Litchfield, J. T. and Wilcoxon, F., J. Pharmacol. Sci. 54, (1965) 888.

EXAMPLES

EXAMPLE 1

4.4 g (0.02 moles) of 3-(carboxy-methyl)-6-methyl-4-oxo-4H-pyrido(1,2a)pyrimidine are suspended in 60 ml of glacial acetic acid and hydrogenated under atmospheric pressure in the presence of 1.5 g of charcoal.

The calculated hydrogen quantity is absorbed within 30 minutes, whereafter the catalyst is filtered off and the solution evaporated to dryness in vacuo. The 8.2 g of the residual oil is recrystallized from 9 ml of 96% alcohol. 3.3 g (75%) of the white colored 3-(carboxy-methyl)-6-methyl-4-oxo-6,7,8,9-tetrahydro-4h-pyrido(1,2a)pyrimidine are obtained, melting at 193°–194° C. The melting point remains unchanged on recrystallization.

Analysis:
Calculated: C: 59.45%; H: 6.35%; N 12.6%; Found: C: 59.81%; H: 6.22%; N: 12.58%.

EXAMPLE 2

6.0 g (0.15 moles) of sodium hydroxide are dissolved in 60 ml of water. In the solution thus obtained 14.4 g (0.05 miles) of 3-(ethoxycarbonyl-methyl)-6-methyl-4-oxo-6,7,8,9-tetrahydro-4H pyrido(1,2a)pyrimidine hydrochloride are added and the solution is stirred at room temperature for 3 hours, whereafter the pH value is adjusted with hydrochloric acid 1:1 (about 8 ml) to 7 and the solution is decolorized with charcoal. The pH value of the decolorized solution is adjusted to 4 (at a lower pH value the acid is dissolved). The solution is allowed to stand for some hours in a refrigerator, and the precipitated crystals are filtered. 3.6 g (32%) of the 3-(carboxy-methyl)-6-methyl-4-oxo-6,7,8,9-tetrahydro-4H-pyrido(1,2a)pyrimidine are obtained, melting at 191° C. The aqueous mother-liquor is evaporated and the residue of 10 g is dissolved in 20 ml of water by heating. On cooling 3.5 g (30%) of the acid, melting at 192° C. are obtained. The total yield is 7.1 g (62%). The melting point rises to 193°–194° C. when recrystallizing from 96% alcohol. The crystals thus obtained do not give any melting point depression with the product obtained according to Example 1.

When using in the method described above the 3-(ethoxycarbonyl-methyl)-4-oxo-6,7,8,9-tetrahydro-4H-pyrido(1,2a)-pyrimidine as starting material the 3-(carboxy-methyl)-4-oxo-6,7,8,9-tetrahydro-4H-pyrido(1,2a)pyrimidine is obtained melting at 174°–175° C. with a yield of 80%.

EXAMPLE 3

53.7 g (0.2 moles) of 3-(ethoxycarbonyl-methyl)-4-oxo-4H-pyrido(1,2a)pyrimidine hydrochloride are dissolved in 250 ml of water. After addition of 10 ml of hydrochloric acid and 20 g of palladium-charcoal catalyst the hydrogenation is carried out at a pressure of 5–10 atmosphere. After the calculated quantity of hydrogen is adsorbed, the catalyst is filtered and the pH value is adjusted to 7 by the addition of a sodium carbonate solution of 20%, The solution obtained is decolorized with charcoal and filtered. The clear solution is extracted 3 times with 300 ml. of benzene. The unified extracts are dried on sodium sulphate; the solution is filtered and the filtrate evaporated to dryness. 32.0 g (68%) of a crystalline product are obtained, melting at 63°–66° C. Extracting the aqueous mother-liquor with chloroform and working up the extract obtained, further 2.8 g (5.5 5) of the product are obtained, total yield 73.5%. Recrystallizing the product from a mixture of alcohol-petro ether the snow-white 3-(ethoxycarbonyl-methyl)-4-oxo-6,7,8,9-tetrahydro-4H pyrido (1, 2a) pyrimidine is obtained, melting at 65°–66° C.

Analysis:
Calculated: C, 61.0%; H, 6.75%; N, 11.86%; Found C, 60.01%; H, 6.82%; N, 12.02%.

When using a 3-(ethoxycarbonyl-methyl)-7-methyl-4-oxy-4H-pyrido(1,2a)pyrimidine-hydrochloride as starting material, 3-(ethoxycarbonyl-methyl)-7-methyl-4-oxo-6,7,8,9-tetrahydro-4H-pyrido(1,2a)pyrimidine is obtained in the form of a non-crystallizable oil. The melting point of the hydrochloride amounts to 146°–147° C.

When using for starting material the 3-(ethoxycarbonylmethyl)-8-methyl-4-oxo-4H-pyrido(1,2a)pyrimidine-hydrochloride the 3-(ethoxycarbonyl-methyl)-8-methyl-4-oxo-4H-pyrido(1,2a) pyrimidine is obtained, melting at 44°–45° C.

EXAMPLE 4

025 g (1 mmol) of 3-(ethoxycarbonyl-methyl)-6-methyl-4-oxo-6,7,8,9-tetrahydro-4H-pyrido(1,2a)pyrimidine are dissolved in 1 ml absolute alcohol and 0.1 ml (2 mmoles) of 100% hydrazine hydrate are added. After standing for 1 day at room temperature the solution is evaporated to dryness and the remaining, slowly crystallizing product is recrystallized from an alcohol-ether mixture. 0.17 g (72R) of the white colored 6-methyl-4- oxo-6,7,8,9-tetrahydro-4H-pyrido(1,2a)pyrimidine-3-(methyl-carbonhydrazide) are obtained, melting at 132°–133° C.

The melting point does not change after recrystallization.

Analysis:
Calculated: C, 55.91%; H, 6.83%; N, 23.72%; Found: C, 55.20%; H, 7.15%; N, 23.69%.

EXAMPLE 5

25.0 g (0.1 mole) of 3-(ethoxycarbonyl-methyl)-6-methyl-4-oxo-6,7,8,9-tetrhydro-4H-pyrido(1,2a)pyrimidine are dissolved in 50 ml. of absolute acetone and 13.2 g (0.105 moles) of freshly distilled dimethyl sulphate are added to the solution. The solution is kept for 10 minutes at 40° C. and allowed to stand at room temperature. The next day the precipitated crystals are filtered and washed with a small quantity of absolute acetone. The product obtained is recrystallized from a double quantity of absolute alcohol. Thus 21 g (56%) of the white colored 3-(ethoxy-carbonyl-methyl)-1,6-dimethyl-4-oxo-6,7,8,9-tetrahydro-4H-pyrido(1,2,a)-pyrimidinium methosulphate are obtained, melting at 150° C. The melting point does not vary on recrystallization.

Analysis:
Calculated: C, 47.86%; H, 3.75%; N, 7.44%; S, 8.52%; Found: C, 47.98%; H, 3.70%; N, 7.42%; S, 8.41%.

When using in the process described above the 3-(tehoxy-carbonyl-methyl)-4-oxo-6,7,8,9-tetrahydro-4H-pyrido(1,2a)-pyrimidine as starting material, the 3-(ethoxycarbonyl-methyl)-1-methyl)-1-methyl-4-oxo-6,7,8,9-tetrahydro-4H-pyrido-(1,2a)pyridiminium methosulphate is obtained, melting at 141°–142° C.

EXAMPLE 6

In an apparatus provided with a stirrer 111.1 g (0.5 moles) of 3-(carboxymethyl)-6-methyl-4-oxo-6,7,8,9-tetrahydro-4H-pyrido(1,2a)pyrimidine are heated by means of an oil-bath of 220°–230° C. for 1 hour, while the $CO_2$ development ceases gradually. The residue is fractionated in vacuo at a pressure of 0.3–0.4 Hgmm. On cooling and scraping 61.5 g (69%) of a crystallizing oil are obtained. On recrystallizing the crystals obtained from a half quantity of ethyl acetate the white colored 3,6-dimethyl-4-oxo-6,7,8,9-pyrido(1,2a)pyrimidine is obtained, melting at 73°–74° C.

The melting point does not vary on recrystallization.
Analysis:
Calculated: C, 67.39%; H, 7.92%; N, 15.72%; Found: C, 67.1%; H, 8.2%; N, 15.91%.

EXAMPLE 7

In an apparatus provided with a water-separating column 22.2 g (0.1 mole) of 3-(carboxymethyl)-6-methyl-4-oxo-6,7,8,9-tetrahydro-4H-pyrido(1,2a)pyrimidine, 12.1 g (0.1 mole) of 2-phenyl-ethylamine and 100 ml. of xylene are refluxed for 3 hours, while 1.8 ml of water are collected in the condenser. The solution is then evaporated to dryness. 32.2 g (99%) of the 3-(N-2-phenylethyl)-carboxamido-methyl-6-methyl-4-oxo-6,7,8,9-tetrahydro-4H-pyrido(1,2a)pyrimidine are obtained in the form of a not crystallizing oil. On dissolving 3.35 g (0.01 mole) of the oil in 3 ml of alcohol and adding to the solution obtained 1.5 ml of a 70% perchloric acid, 3.0 g (71%) of the pale-yellow colored 3-(N-2-phenyl-methyl)-carboxamido-methyl-6-methyl-4-oxo-6,7,8,9-tetrahydro-4H-pyrido(1,2a)-pyrimidinium perchlorate are obtained, melting at 174°–176° C. The melting point rises after recrystallization from a 8-fold quantity of ethanol to 176°–177° C.

Analysis:
Calculated: C, 53.59%; H, 5.68%; N, 9.87%; Cl, 8.32%; Found: C, 53.61%; H, 5.65%; N, 9.94%; Cl, 8.95%.

On using in the process above 2-(3,4-dimethoxyphenyl)-ethyl amine as an amine component, 3-(N-2-(3,4-dimethoxy-phenyl)-ethyl)-carboxamide-methyl-6-methyl 1-4-oxo-6,7,8,9-tetrahydro-4H-pyrido(1,2a)-pyrimidine is obtained with a yield of 99% in in the form of a not crystallizing oil.

EXAMPLE VIII

The same procedures and reaction conditions as in Example I are employed except that 0.02 moles of 3-(carboxymethyl)-6,7,8,9-dimethyl-4oxo-4H-pyrido (1,2a) pyrimidine are the starting material and the end product is 3-(carboxymethyl)-6,7-dimethyl-4-oxo-6,7,8,9-tetrahydro-4H-pyrido(1,2a)pyrimidine.

EXAMPLE IX

The same procedures and reaction conditions as in Example I are employed except that 0.02 moles of 3-(carboxymethyl)-6-methyl, 7-chloro-4-oxo-4H-pyrido(1,2A) pyrimidine are the starting material and the end product is 3-(carboxymethyl)-6-methyl, 7-chloro-4-oxo-6,7,8,9-4H-pyrido(1,2a)pyrimidine.

EXAMPLE X

The same procedures and reaction conditions as in Example I are employed except that 0.02 moles of 3-(carboxymethyl)-6-methyl, 7-benzyl-4-oxo-4H-pyrido(1,2a)pyrimidine are the starting material and the end product is 3-(carboxymethyl)-6-methyl,7-benzyl-4-oxo-6,7,8,9-tetrahydro-4H-pyrido(1,2a)pyrimidine.

EXAMPLE XI

The same procedures and reaction conditions as in Example 1 are employed except that 0.02 moles of 3-(carboxymethyl)-6-methyl, 7-amino-4-oxo-4H-pyrido(1,2a) pyrimidine are the starting material and the end product is 3-(carboxymethyl)-6-methyl, 7-amino-4oxo-6,7,8,9-tetrahydro (1,2a) pyrimidine.

EXAMPLE XII

The same procedures and reactions as in Example 1 are employed except that 0.02 moles of 3-(carboxymethyl)-6-methyl, 7-methylamino-4-oxo-4H-pyrido(1,2a) pyrimidine are the starting material and the end product is 3-(carboxymethyl)-6-methyl, 7-methylamino-4-oxo-6,7,8,9-tetrahydro-4H-pyrido(1,2a) pyrimidine.

EXAMPLE XIII

The same procedures and reaction conditions as in Example 1 are employed except that 0.02 moles of 3-(carboxymethyl)-6-methyl, 7-acetylamino-4-oxo-4H-pyrido (1,2a) pyrimidine are the starting material and the end product is 3-(carboxymethyl)-6-methyl, 7-actylamino-4-oxo-6,7,8,9,-tetrahydro-4H-pyrido (1,2a) pyrimidine.

EXAMPLE XIV

The same procedures and reaction conditions as in Example I are employed except that 3-(carboxymethyl)-6-methyl-7-hydroxy-4-oxo-4H-pyrido (1,2a) pyrimidine are the starting material and the end product is 3-(carboxymethyl)-6-methyl, 7-hydroxy-4-oxo-6,7,8,9-tetrahydro-4H-pyrido (1,2a)pyrimidine.

EXAMPLE XV

The same procedures and reaction conditions as in Example 1 are employed except that 3-(carboxymethyl)-6-methyl, 7-methoxy-4-oxo-4H-pyrido (1,2a) pyrimidine are the starting material and the end product is 3-(carboxymethyl)-6-methyl, 7-methoxy-4-oxo-6,7,8,9-tetrahydro-4H-pyrido (1,2a) pyrimidine.

EXAMPLE XVI

The same procedures and reaction conditions as in Example 1 are employed except that 3-(carboxymethyl)-6-methyl, 7-carboxy-4-oxo-4H-pyrido (1,2a) pyrimidine are the starting material and the end product is 3-(carboxymethyl)-6-methyl, 7-carboxy-4-oxo-6,7,8,9-tetrahydro-4H-pyrido (1,2a) pyrimidine.

EXAMPLE XVII

The same procedures and reaction conditions as in Example I are employed except that 0.02 moles of 3-(carboxymethyl)-6-methyl, 7-carboxamido-4-oxo-pyrido (1,2a) pyrimidine are the starting material and the end product is 3-(carboxymethyl)-6-methyl, 7-carboxamido-4-oxo-6,7,8,9-tetrahydro-4H-pyrido (1,2a) pyrimidine.

We claim:
1. 3-(ethoxycarbonyl-methyl-6-methyl-4-oxo-6,7,8,9-tetrahydro-4H-pyrido-(1,2a)-pyrimidine.

* * * * *